United States Patent [19]

Verhoeven

[11] Patent Number: 4,697,037

[45] Date of Patent: Sep. 29, 1987

[54] PREPARATION OF DIBENZO[B,F]THIEPIN COMPOUNDS

[75] Inventor: Thomas R. Verhoeven, Cranford, N.J.

[73] Assignee: Merck & Co., Inc., Rahway, N.J.

[21] Appl. No.: 786,768

[22] Filed: Oct. 11, 1985

Related U.S. Application Data

[63] Continuation of Ser. No. 610,064, May 14, 1984, abandoned.

[51] Int. Cl.[4] .................. C07C 149/40; C07C 149/42; C07C 51/15; C07C 147/13

[52] U.S. Cl. ...................................... 562/432; 558/413; 558/416; 562/423; 562/429; 562/430

[58] Field of Search ............... 562/423, 432, 429, 430; 558/416

[56] References Cited

U.S. PATENT DOCUMENTS

| | | | |
|---|---|---|---|
| 3,450,771 | 6/1969 | Dombro | 562/432 X |
| 3,560,531 | 2/1971 | Normant | 562/423 X |
| 3,651,106 | 3/1972 | Harrison | 562/423 X |

OTHER PUBLICATIONS

Gilman et al., J. Org. Chem., 22, 1715–1716 (1957).
Org. Reactions, 26, 74–75, Wiley & Sons (1979).
Stoyanovich et al., Angew. Chem. Int. Ed., 5, 127 (1966).
Org. Reactions, 26, 61–64, Wiley & Sons (1979).
Bailey et al., J. Chem. Soc. B 1446–1449 (1971).
Chiba et al., Chem. Abst. vol. 90, Abstract No. 121271f, 1979.
Fieser et al., Reagents for Organic Synthesis, vol. 3, pp. 184–185, Wiley-Interscience, N.Y., 1972.
Rembaum et al., Am. Chem. Soc., Div. Polymer Chem. Preprints, vol. 3, No. 2, 1962, pp. 251–262.
Valenta et al., Chem. Abst., vol. 92, Abstract No. 128853x, 1980.

*Primary Examiner*—Donald B. Moyer
*Assistant Examiner*—Patricia M. Scott
*Attorney, Agent, or Firm*—Gabriel Lopez; Hesna J. Pfeiffer

[57] ABSTRACT

The preparation of dibenzo[b,f]thiepin compounds by a process comprising the direct carboxylation of an ortho-toluyl-aryl sulfide to introduce a phenylacetic acid side chain is disclosed.

17 Claims, No Drawings

PREPARATION OF DIBENZO[B,F]THIEPIN COMPOUNDS

This is a continuation of application Ser. No. 610,064, filed May 14, 1984, abandoned.

The present invention relates to the preparation of dibenzo[b,f]thiepin and derivatives thereof. Such compounds are prostaglandin antagonists or important intermediates in preparing prostaglandin antagonists. Examples of prostaglandin antagonists that may be prepared using the methods of the present invention are disclosed in U.S. Pat. No. 4,237,160, U.S. Ser. No. 396,452, filed July 8, 1982, and European Pat. No. 0011067, issued Apr. 21, 1982, these disclosures being hereby incorporated herein by reference.

One embodiment of the present invention relates to a process for the preparation of dibenzo[b,f]thiepin and derivatives thereof comprising direct carboxylation of an ortho-toluylaryl sulfide to introduce a phenylacetic acid side chain. This transformation generally functions as the crucial step in the synthesis of dibenzo[b,f]thiepin compounds. In the process of the present invention, a single high yielding carboxylation step replaces the low yielding multi-step procedure of the prior art.

Prior art syntheses of compounds containing the dibenzo[b,f]thiepin skeleton (see, for example, U.S. Pat. No. 4,237,160 and M. Rajsner et al., Collection of Czechoslov. Chem. Commun., 42, 3079–3093 (1977) suffer from the non-availability and/or expensive nature of functionalized orthohalo-phenylacetic acid derivatives which are required as starting materials. The preparation of these starting materials is inefficient and multistep. The present invention obviates their use and allows the employment of readily available ortho-halo-toluic acid derivatives.

In the process of the present invention, and unlike previous methods, the phenylacetic acid side chain is prepared after the diaryl sulfide linkage has been established. This introduces a greater flexibility in the synthesis of the dibenzo[b,f]thiepin skeleton and permits the use of less costly, commercially available starting materials. Also, this direct carboxylation approach establishes the phenylacetic acid side chain in a single, high yielding step.

In one of its embodiments, the present invention relates to a process for preparing a compound of the formula I:

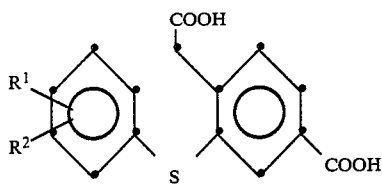

wherein $R^1$ and $R^2$ are independently selected from hydrogen, halogen (i.e. fluorine, chlorine, bromine or iodine), alkyl of 1 to 4 carbon atoms, alkoxy of 1 to 4 carbon atoms, alkylthio wherein the alkyl moiety has 1 to 4 carbon atoms, alkylsulfinyl wherein the alkyl moiety has 1 to 4 carbon atoms, alkyl sulfonyl wherein the alkyl moiety has 1 to 4 carbon atoms, trifluoromethyl, trifluoromethylthio, cyano, nitro, dialkylamino wherein each alkyl moiety has 1 to 4 carbon atoms, carboxy, and phenylalkyl wherein the alkyl moiety has 1 to 4 carbon atoms, substituted phenylalkyl wherein the alkyl moiety has 1 to 4 carbon atoms and the phenyl group is substituted with halogen, nitro, alkyl having 1 to 4 carbon atoms, said process comprising treating a dianion of the formula II:

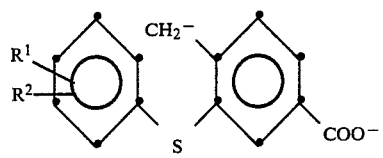

wherein $R^1$ and $R^2$ are as defined above with carbon dioxide, preferably at a temperature of −40° to 0° C., more preferably at a temperature of −20° C. The pressure should be one atmosphere but a higher pressure could be used. The solvent should be an inert solvent and is preferably an ether solvent such as tetrahydrofuran, 1,2-dimethoxyethane (glyme), diglyme or ethyl ether, and is more preferably a 20 to 1 mixture (by volume) of tetrahydrofuran and 1,3-dimethylimidazolidinone.

In a preferred embodiment of the present invention, $R^1$ and $R^2$ are independently selected from hydrogen and halogen.

The aforementioned dianion may be formed from a compound of the formula III:

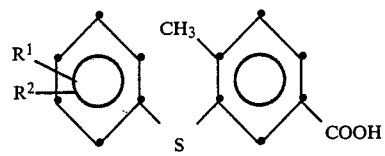

wherein $R^1$ and $R^2$ are as defined above by initially forming a carboxylate salt with a base for example, sodium hydride, followed by deprotonation. Deprotonation may be accomplished with an alkali metal dialkylamide base (for example, lithium diethylamide), an alkylamide base (for example, ethyl amide or isopropyl amide), or an alkali metal amide base, (for example, lithium or sodium amide). The preferred base is lithium diisopropylamide. The preferred temperature is −40° to −10° C. A temperature of −20° C. is more preferred. The temperature of the reaction medium may be maintained at −40° C. to 0° C. The pressure is preferably, atmospheric, but a higher pressure could be used. The solvent should be an inert solvent and is preferably an ether solvent such as tetrahydrofuran, 1,2-dimethoxyethane (glyme), diglyme or ethyl ether, and is more preferably a 20 to 1 mixture (by volume) of tetrahydrofuran and 1,3-dimethylimidazolidinone. Preferably, the dianion that is prepared from the aforementioned compound of the Formula III is not isolated and one immediately proceeds to convert the dianion of the Formula II to the desired compound of the Formula I.

In view of the fact that the carboxylation reaction may be difficult when $R^1$ and $R^2$ are bromine, iodine, alkylthio, alkyl sulfinyl, alkyl sulfonyl or nitro, compounds of the Formula II (and the compounds of the Formula III from which they are prepared) having such substituents are less preferred as starting materials.

The process of the present invention is also applicable to compounds wherein $R^1$ and $R^2$ are independently selected from amino, alkanoyl of 1 to 4 carbon atoms, hydroxyl, thio, alkylamino wherein the alkyl moiety has 1 to 4 carbon atoms, hydroxyalkyl wherein the alkyl moiety has 1 to 4 carbon atoms, mercapto, substituted phenylalkyl wherein the alkyl moiety has 1 to 4 carbon atoms and the phenyl group is substituted with amino or hydroxy. For such compounds, however, these functional groups should be protected prior to the carboxylation reaction.

The following reaction scheme showing the synthesis of 2-(3'-fluorophenylthio)-4-carboxyphenylacetic acid which is an intermediate in the production of S-7-fluorodibenzo[b,f]thiepin-3-carboxylic acid-5-oxide illustrates the importance of the process of the present invention:

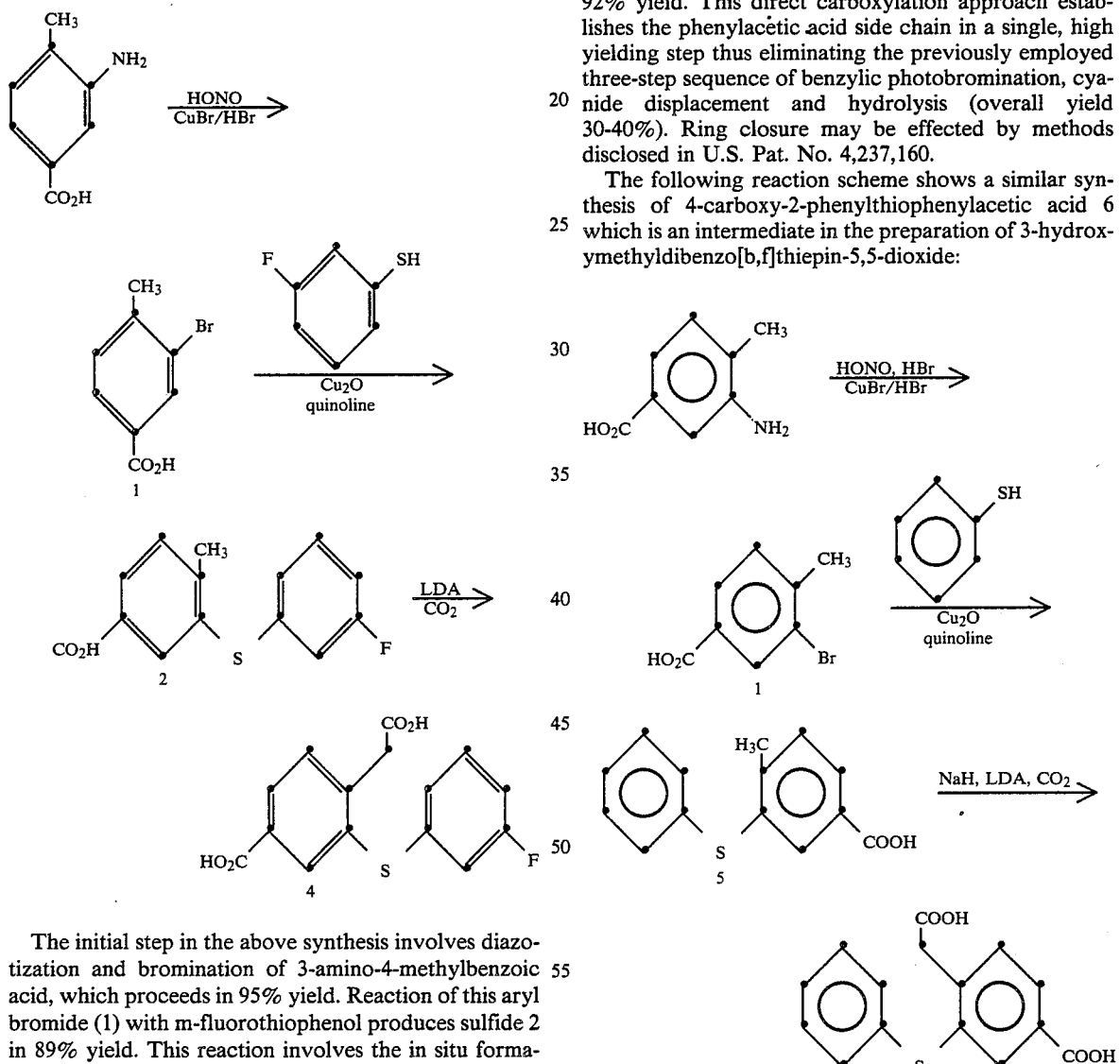

The initial step in the above synthesis involves diazotization and bromination of 3-amino-4-methylbenzoic acid, which proceeds in 95% yield. Reaction of this aryl bromide (1) with m-fluorothiophenol produces sulfide 2 in 89% yield. This reaction involves the in situ formation of 3-fluorophenylthiocopper (ArSCu) with cuprous oxide which subsequently couples with the aryl bromide at 180–190° C. Incorporation of the diaryl sulfide linkage at this early stage in the process results in improved yields and elimination of side reactions compared to the prior art process. Employment of the readily available aryl bromide 1 obviates the use of iodide or bromide 3, an economically unattractive intermediate in the prior art synthesis.

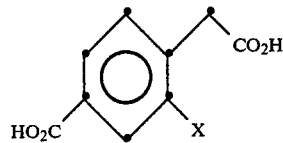

X = Br, I

The crucial carboxylation of 2 is accomplished in a single step via its dianion. The dianion is generated by initial formation of the carboxylate salt with sodium hydride with final benzylic deprotonation being accomplished with lithium diisopropylamide at −20° C. Treatment with carbon dioxide produces diacid 4 in 92% yield. This direct carboxylation approach establishes the phenylacetic acid side chain in a single, high yielding step thus eliminating the previously employed three-step sequence of benzylic photobromination, cyanide displacement and hydrolysis (overall yield 30-40%). Ring closure may be effected by methods disclosed in U.S. Pat. No. 4,237,160.

The following reaction scheme shows a similar synthesis of 4-carboxy-2-phenylthiophenylacetic acid 6 which is an intermediate in the preparation of 3-hydroxymethyldibenzo[b,f]thiepin-5,5-dioxide:

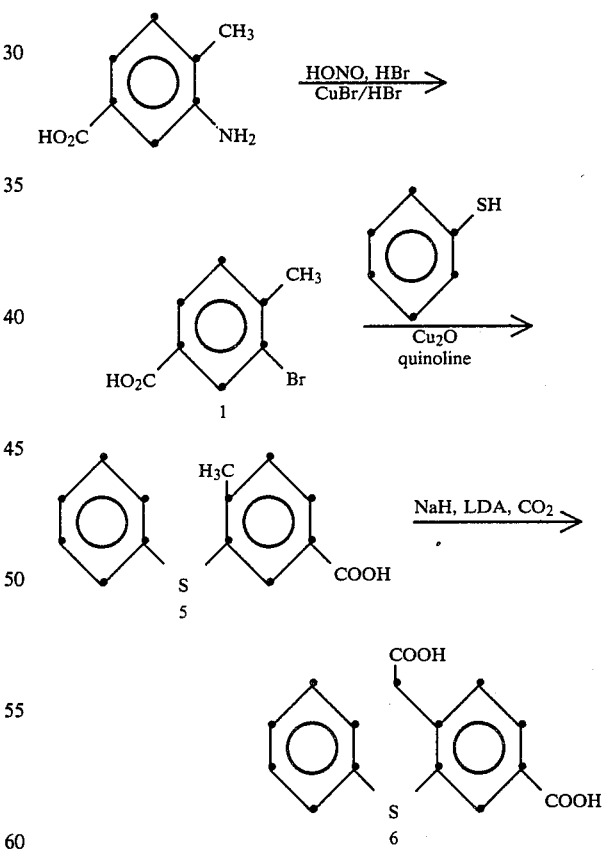

Reaction of 3-bromo-4-methylbenzoic acid 1 with thiophenol and cuprous oxide in quinoline at 180° C produces 3-phenylthio-4-methylbenzoic acid 5 in 95–96% yield. Generation of the dianion of 5 is ccomplished by sequential treatment with sodium ydride and then lithium diisopropylamide in a olvent mixture of tetrahydrofuran and 1,3-dimethylmidazolidinone at −20° C. Carboxylation at −15° with carbon dioxide at a pressure of one atmosphere produces the diacid 6 in 90% yield.

The following Examples are illustrative of the present invention:

EXAMPLE 1

Preparation of 2-(3′-Fluorophenylthio)-4-carboxyphenylacetic acid

Step A: 3-Bromo-4-methylbenzoic acid

A 22 liter 3-necked, round bottom flask, fitted with an overhead stirrer, thermometer, and a 2 liter addition funnel was charged with water (6.4 liters) and 3-amino-4-methylbenzoic acid (2.1 kg, 13.89 mole) to produce a thick slurry. While cooling the mixture in an ice/water bath, concentrated hydrochloric acid (1.76 liters) was added over a 5 minute period. The internal temperature rose to 35° C. during this addition. The mixture was recooled to −3° C. with an aqueous ethanol/dry ice bath and a solution of sodium nitrite (1006 g, 14.58 mole) dissolved in water (1.4 liters) was added over a 1 hour period, maintaining the temperature between −3° and 0° C. During the final stages of the addition, gas evolution and consequent foaming were observed. Care should be exercised to maintain the cooling bath temperature at no lower than −10° C. Below that temperature significant precipitation of the diazonium salt occurs thereby hampering its transferral from the reaction vessel.

Meanwhile, a 30 gallon, polypropylene vat, equipped with an overhead stirrer, and a 3 liter, jacketed, brine-cooled addition funnel was charged with 48% hydrobromic acid (19 liters) and cuprous bromide (3.52 kg, 24.53 mole) and heated to 30°–35° C in a water bath. The cold diazonium salt solution was transferred in portions to the brine-cooled addition funnel (to maintain the temperature of the diazonium hydrochloride solution at 0° C.) and added to the vigorously stirred cuprous bromide solution over about 1.5 hours, maintaining a reaction temperature of 35–40° C. and adding diethyl ether periodically in 100 to 300 ml portions with a total volume of about 800 ml being added, in order to reduce the volume of foam caused by nitrogen evolution. Nitrogen evolution subsided and the mixture was stirred at ambient temperature overnight.

The product was recovered from the reaction mixture by suction filtration. The filter cake was sucked completely dry because addition of water to the unfiltered reaction mixture precpitates highly water insoluble copper salts which are difficult to remove. The filter cake was washed with sufficient water until neutral (as tested with alk-acid paper) and the product was air-dried at 70°–75° C. overnight to provide a tan solid (2811 g, 94.1%), mp 203°–205° C.

Recrystallization of a sample from aqueous ethanol provided cream colored needles, mp 206°–207.5° C.

Analysis of the product (prior to recrystallization) by HPLC (reverse phase, Altex, ultraspohereoctyl, 5 micron, 25 cm×4.6 mm I.D., $CH_3CN:H_2O$, 50:50 v/v with 0.1% $H_3PO_4$, flow rate=2.0 ml/minute) indicated an impurity (retention time=2.0 minutes) of 8–10% (based on UV absorbance at 254 nm). The retention time of the product is 4.2–4.3 minutes. This impurity is believed to be 3-hydroxy-4-methyl benzoic acid based upon expected competitive side processes.

STEP B: 3-(3′-Fluorophenylthio)-4-methylbenzoic acid

A 22 liter, 3-necked round bottom flask, fitted with an overhead stirrer, thermometer, and a distillation head was placed in a heating mantle and charged with quinoline (6 liters), 3-bromo-4-methylbenzoic acid (2.725 kg, 12.67 mole), m-fluorothiophenol (1.70 kg, 13.28 mole) and cuprous oxide (958 g, 6.69 mole). Due to its pervasive stench, the m-fluorothiophenol was transferred in a fume hood. The reaction of 3-bromo-4-methylbenzoic acid and m-fluorothiophenol with quinoline was exothermic causing a temperature rise to 75° C. The red slurry was placed under a nitrogen blanket and heated with stirring to 180–190° C. over a 1 hour period collecting the water as it distilled. When the internal temperature reached 110° C., the mixture became very thick and distillation of water commenced. This thickening was caused by the formation and precipitation of (m-fluorothiophenyl)copper. Continued heating slowly redissolved this precipitate with the mixture becoming completely homogeneous at a temperature of 150° C. This temperature range was maintained for 0.5 hour. The progress of the coupling may be conveniently monitored by reverse phase HPLC (Altex, ultrasphere-octyl, 5 micron, 25 cm×4.6 mm I.D., 50:50, volume/volume, $CH_3CN:H_2O$ with 0.1% $H_3PO_4$, 2 ml/minute). Retention time; 3-bromo-4-methylbenzoicacid: 4.2–4.3 minute, 3-(3′-fluorophenylthio)-4-methylbenzoic acid: 9.7–10.0 minute. The black mixture was allowed to cool to 110° C. and then transferred to a stirred solution of 6N hydrochloric acid (28 liters).

After stirring overnight, the crude product was collected by suction filtration and washed with 6N hydrochloric acid (19 liters), and then with water until the filtrate was neutral (alk-acid paper). The filter cake was washed with five 1 liter portions of isopropanol and air-dried overnight at 40° C. to provide the title compound as a dark tan solid (2785 g, 83.8%) mp 154–158° C. Recrystallization of a sample from toluene yielded white needles, mp 162–163° C.

Analysis for $C_{14}H_{11}FO_2S$, calculated: C:64.11; H:4.20; S:12.22; F:7.24. found: C:64.25; H:4.23; S:12.29; F:7.38.

Quantitative HPLC assay of this material (prior to recrystallization) using column conditions as described above in this paragraphs, indicated a product purity of 95%.

The isopropanol filtrate was concentrated to dryness, dissolved in acetone (2 liter) and treated with charcoal (82 g) for 30 minutes. Filtration through celite and concentration under vacuum provided a dark solid which was crystallized from hot toluene (2 liter) to yield a second crop of product as tan needles (305 g, 9.2%) mp 140–144° C. Both crops were suitable for use directly in the subsequent transformation.

If desired, an alternative procedure may be used to obtain material of higher melting point. This involves azeotropically drying the water-washed filter cake with toluene and subsequent crystallization from a minimum volume of hot toluene (approximately 200 g/liter). When this modification was performed on a reaction involving 1660 g (7.72 mole) of 3-bromo 4-methylbenzoic acid a first crop of 1631 g (80.8%), mp 161.5–163° C. and a second crop of 124 g (6.1%), mp 158–161° C. were obtained for a combined yield of 86.9%.

STEP C:
2-(3′-Fluorophenylthio)-4-carboxyphenylacetic acid

In this step, all glassware was dried via a vacuum purge technique under nitrogen, with all manipulations carried out under an inert atmosphere and the solvents (tetrahydrofuran, 1,3-dimethyl 2-imidazolidinone and diisopropylamine) were all dried over 4 Angstom sieves prior to use.

A dry, 3-necked, 12 liter round bottom flask, equipped with an overhead stirrer, condenser, calibrated addition funnel, thermometer and nitrogen inlet was charged with sodium hydride (202 g, 50% oil dispersion, 4.12 mole), tetrahydrofuran (300 ml) and 1,3-dimethyl-2-imidazolidinone (DMI) (525 ml). A slight out-gassing and color change occurs upon addition of DMI to the sodium hydride. 3-(3′-Fluoropehnylthio)-4-methylbenzoic acid (1050 g, 4.01 mole) was dissolved in tetrahydrofuran (2300 ml) under nitrogen (endothermic) and slowly added over 2 hours to the sodium hydride slurry with vigorous stirring. Addition at this rate maintained the internal temperature between 55°–60° C. Hydrogen evolution subsided and the mixture was allowed to cool slowly. The color of the reaction mixture at this stage may vary from golden yellow to black depending on the quality of the starting sulfide.

Meanwhile, a dry, 3-necked, 22 liter round bottom flask, equipped with an addition funnel, thermometer, nitrogen inlet and overhead stirrer was charged with tetrahydrofuran (8.0 l) and diisopropylamine (725 ml, 5.17 mole). The source and quality of the THF employed here is crucial. Fisher reagent grade tetrahydrofuran provided a clear yellow solution of lithium diisopropylamide. An inferior tetrahydrofuran might produce black colored mixtures of lithium diisopropylamide, unsuitable for use in this reaction. The integrity of the THF-diisopropylamine solution may be tested by treating a sample with n-butyllithium prior to proceeding with the entire batch.

The stirred solution was cooled to −30° C. in an acetone/dry ice bath and n-butyllithium (3125 ml, 5.06 mole, 1.62M in hexane) was added over 15 minutes. n-Butyllithium is commercially available in 5 gallon steel cylinders from Lithium Corporation of America and may be conveniently dispensed directly into the calibrated addition funnel immediately prior to its introduction to the reaction vessel. The temperature rose to −10° C. and a clear yellow solution resulted. The solution was re-cooled to −40° C. and the earlier prepared sulfide solution was added over 15 minutes, producing an opaque mixture. The cooling bath was removed, and the temperature allowed to rise to −20° C. On a large scale, the otherwise slow warm-up may be hastened by immersing the reaction vessel in cold water. Carbon dioxide (bone dry gas) was rapidly bubbled through the reaction mixture with vigorous stirring for 1.5 hours. The opaque mixture decolorized producing a cream-colored precipitate.

Isopropanol (200 ml) was carefully added to consume any excess sodium hydride or lithium diisopropylamide present, then 1 liter of water was carefully added over about 15 minutes. The reaction mixture darkened and layer separation occured. The mixture was transferred to a large extractor, diluted with an additional 3.5 l of water and stirred for 15 minutes. The lower aqueous layer was removed and the organic phase washed with 5% aqueous sodium hydroxide (1.6 liters). The total aqueous extracts were combined and acidified with vigorous stirring with concentrated hydrochloric acid (approximately 1.5 liters). The product separated as a solid. If oiling occurs, stirring is continued and 4 to 5 liters of hexane are added to induce solidification. After 2 hours of vigorous agitation the mixture was filtered, washed with water and air dried at 40° C. to give a cream-colored powder, (1130 g, 92%), mp 200°–203° C.

Recrystallization of a sample from aqueous isopropanol produced white needles, mp 207°–207.5° C.

Analysis for $C_{15}H_{11}FSO_4$: calculated: C:58.81; H:3.62; S:10.47; F:6.20. found: C:58.84; H:3.57; S:10.52; F:6.38.

Quantitative HPLC analysis (reverse-phase, Altex, ultrasphere-octyl, 5 microns, 25 cm×4.6 mm I.D., $CH_3CN:H_2O$, 40:60 v/v with 0.1% $H_3PO_4$, 2 ml/minute, 254 nm) indicated a purity of 87–89%.

EXAMPLE 2

4-carboxy-2-phenylthiophenylacetic acid

Step A: 4-Methyl-3-phenylthiobenzoic acid

A 22 liter 3-necked round bottom flask, fitted with an overhead stirrer, thermometer, and a distillation head was placed in a heating mantle and charged with quinoline (6 liter), 3-bromo-4-methylbenzoic acid (2.75 kg, 12.79 mole), thiophenol (1.75 kg 15.22 mole) and cuprous oxide (958 g, 6.7 mole). The red slurry was placed under a nitrogen blanket and heated with stirring to 180°–200° C. over a 1 hour period collecting the water as it distills. This temperature was maintained for 0.5 hours. The mixture was cooled to 110° C. and then transferred to a stirred solution of 6N hydrochloric acid. After stirring overnight, the product was collected by suction filtration, washed with 6N hydrochloric acid (19 liters) and then with water until neutral (alk-acid paper). The filter cake was washed with isopropanol and dried at 40° C. in vacuo to yield the title compound as a tan solid (2.97 kg, 95% yield, 91% purity).

Step B: 4-Carboxy-2-phenylthiophenylacetic acid

A dry 3-necked, 12 liter round bottom flask, equipped with an overhead stirrer, condenser, calibrated addition funnel, thermometer and nitrogen inlet was charged with sodium hydride (202 g, 50% oil dispersion, 4.12 mole), tetrahydrofuran (300 ml) and 1,3-dimethyl-2-imidazolidinone (DMI) (525 ml). 3-Phenylthio-4-methylbenzoic acid (980 g, 4.01 mole) is dissolved in tetrahydrofuran (2300 ml) under nitrogen (endothermic) and slowly added over 2 hours to the sodium hydride slurry with vigorous stirring. Addition at this rate maintains the internal temperature between 55° and 60° C. Hydrogen evolution subsided and the mixture was allowed to cool slowly.

Meanwhile, a dry 3-necked, 22 liter round bottom flask, equipped with an addition funnel, thermometer, nitrogen inlet and overhead stirrer was charged with tetrahydrofuran (8.0 l) and diisopropylamine (725 ml, 5.17 mole). The stirred solution was cooled to −30° C. and n-butyllithium (3125 ml, 5.06 mole, 1.62 M in hexane) was added over 15 minutes. The temperature increased to −10° C. and a clear yellow solution resulted. The solution was re-cooled to −40° C. and the earlier prepared sulfide solution was added over 15 minutes, producing an opaque mixture. The cooling bath was removed, and the temperature allowed to rise to −20° C. and aged for 10 minutes. Carbon dioxide (bone dry gas) was passed over the surface of the reaction mixture with vigorous stirring for 1.5 hours. The opaque mixture decolorized producing a cream-colored precipitate.

Isopropanol (200 ml) was carefully added to consume any excess sodium hydride or lithium diisopropylamide present, then 1 liter of water was carefully added over about 15 minutes. The reaction mixture darkened and layer separation occured. The mixture was transferred to a large extractor, diluted with an additional 3.5 l of water and stirred for 15 minutes. The lower aqueous layer was removed and the organic phase washed with 5% aqueous sodium hydroxide (1.6 liters). The total aqueous extracts were combined and acidified with vigorous stirring with concentrated hydrochloric acid (approximately 1.5 liters). The product separated as a solid. If oiling occurs, stirring should be continued and 4 to 5 liters of hexane added to induce solidification. After 2 hours of vigorous agitation, the mixture was filtered, washed with water and air dried at 40° C. to give a tan to cream-colored powder, (1060 g, 92% yield, 92% purity).

What is claimed is:

1. A process for preparing a dianion of the formula II:

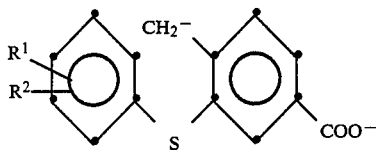

which comprises reacting, in a solvent, sodium hydride with a compound of Formula III:

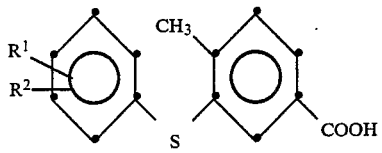

wherein $R^1$ and $R^2$ are independently selected from hydrogen, halogen, alkyl or 1 to 4 carbon atoms, alkoxy of 1 to 4 carbon atoms, alkylthio wherein the alkyl moiety has 1 to 4 carbon atoms, alkylsulfinyl wherein the alkyl moiety has 1 to 4 carbon atoms, alkyl sulfonyl wherein the alkyl moiety has 1 to 4 carbon atoms, trifluoromethyl, trifluoromethylthio, cyano, nitro, dialkylamino wherein each alkyl moiety has 1 to 4 carbon atoms, carboxy, and phenylalkyl wherein the alkyl moiety has 1 to 4 carbon atoms, substituted phenylalkyl wherein the alkyl moiety has 1 to 4 carbon atoms and the phenyl group is substituted with halogen, nitro, or alkyl having 1 to 4 carbon atoms, followed by deprotonation with an alkali metal dialkylamide base, an alkylamide base, or an alkali metal amide base.

2. A process according to claim 1, wherein the temperature of the reaction medium is maintained at $-40°$ to $0°$ C.

3. A process according to claim 2, wherein the temperature is $-20°$ C.

4. A process according to claim 1, wherein the pressure is one atmosphere.

5. A process according to claim 1, wherein the solvent is an ether.

6. A process according to claim 1, wherein the solvent is selected from tetrahydrofuran, glyme, diglyme, ethyl ether and a 20 to 1 mixture, by volume, of tetrahydrofuran and 1,3-dimethylimidazolidinone.

7. A process according to claim 1, wherein $R^1$ and $R^2$ are independently selected from hydrogen and halogen.

8. A process according to claim 1, wherein $R^1$ is hydrogen and $R^2$ is halogen.

9. A process according to claim 1, wherein $R^1$ is hydrogen and $R^2$ is fluorine.

10. A process according to claim 9, wherein the fluorine is in the 31-position.

11. A process according to claim 1, wherein $R^1$ and $R^2$ are hydrogen.

12. A process of claim 1 further comprising treating said dianion with carbon dioxide to produce a compound of formula I:

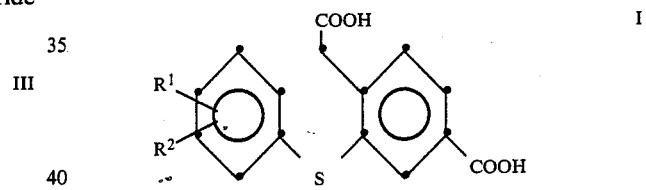

13. A process according to claim 12, wherein the temperature of the reaction medium is maintained at $-40°$ to $0°$ C.

14. A process according to claim 13, wherein the temperature is $-20°$ C.

15. A process according to claim 12, wherein the pressure is one atmosphere.

16. A process according to claim 12, wherein the solvent is an ether.

17. A process according to claim 12, wherein the solvent is selected from tetrahydrofuran, glyme, diglyme, ethyl ether and a 20 to 1 mixture, by volume, of tetrahydrofuran and 1,3-dimethylimidazolidinone.

* * * * *